United States Patent [19]

Inagaki et al.

[11] Patent Number: 5,147,392
[45] Date of Patent: Sep. 15, 1992

[54] PUMPING DRIVE UNIT

[75] Inventors: Yoshitaka Inagaki, Nagoyashi; Akira Suzuki, Nishio; Sadahiko Mushika, Ichinomiya, all of Japan

[73] Assignee: Aisin Seiki K.K., Aichi, Japan

[21] Appl. No.: 434,571

[22] Filed: Nov. 13, 1989

Related U.S. Application Data

[63] Continuation of Ser. No. 176,129, Mar. 31, 1988, abandoned.

[30] Foreign Application Priority Data

Mar. 31, 1987 [JP] Japan .................................. 62-78391
Apr. 7, 1987 [JP] Japan .................................. 62-85084

[51] Int. Cl.$^5$ ........................ A61M 1/10; A61N 1/362
[52] U.S. Cl. .......................................... 623/3; 600/16
[58] Field of Search ................. 128/204.19; 623/3; 600/16, 17, 18

[56] References Cited

U.S. PATENT DOCUMENTS

| | | | |
|---|---|---|---|
| 4,583,525 | 4/1986 | Suzuki et al. | 623/3 |
| 4,794,910 | 1/1989 | Mushika | 600/18 |
| 4,796,606 | 1/1989 | Mushika | 623/3 |
| 4,974,774 | 12/1990 | Nakagawa et al. | 623/3 |

*Primary Examiner*—David Isabella
*Assistant Examiner*—Elizabeth M. Burke
*Attorney, Agent, or Firm*—Sughrue, Mion, Zinn, Macpeak & Seas

[57] ABSTRACT

A pumping unit is disclosed which alternately applies a positive and a negative pressure, both of given values, to aa drive chamber of an artificial heart. In a first and a second embodiment, air of an elevated pressure which is discharged by an air compressor is fed through a positive pressure accumulator and a positive pressure open/close valve to the drive chamber, and a negative pressure from an air decompressor is fed through a negative pressure accumulator and the negative pressure open/close valve to the drive chamber. Alternating open periods are assigned to the positive and the negative pressure open/close valve. During the open period, each valve is opened and closed in a manner corresponding to the prevailing pressure in the drive chamber so as to maintain the pressure at a constant value. In a third embodiment, a positive pressure regulator valve is interposed between the air compressor and the positive pressure accumulator, and the positive pressure open/close valve is interposed between the positive pressure accumulator and the drive chamber while a negative pressure regulator valve is interposed between the air decompressor and the negative pressure accumulator, and the negative pressure open/close valve is interposed between the negative pressure accumulator and the drive chamber. The positive and the negative pressure open/close valves are opened in an alternate fashion. The positive pressure regulator valve is operated with a given duty cycle which depends on the prevailing pressure from the positive accumulator so that such pressure is maintained at a constant value. The negative pressure regulator valve is operated with a given duty cycle which depends on the prevailing pressure of the negative accumulator so that such pressure is maintained at a given value.

2 Claims, 9 Drawing Sheets

| pressure from 23 | signal waveform to energize solenoid 15 | signal |
|---|---|---|
| ① | | 0 |
| ② | | b |
| ③ | | a |
| ④ | | a + b |
| pressure from 23 | signal waveform to energize solenoid 20 | signal |
| ④ | | a + b |
| ⑤ | | a |
| ⑥ | | b |
| ⑦ | | 0 |

PUMPING DRIVE UNIT

This is a Continuation of application Ser. No. 07/176,129 filed Mar. 31, 1988 now abandoned.

FIELD OF THE INVENTION

The invention relates to a pumping drive unit which supplies an alternation of a positive and a negative fluid pressure to a pumping unit which is effective to pump another kind of fluid in response to such alternation, and more particularly, to a control over the driving pressure of the drive unit associated with an artificial heart.

BACKGROUND OF THE INVENTION

By way of example, U.S. Pat. No. 4,546,760 issued to Suzuki et al discloses an artificial heart driving apparatus which alternately supplies an air of a given positive pressure and a suction of a given negative pressure. Air discharged from an air compressor is fed through a first positive pressure open/close valve to a positive pressure accumulator, the pressure of which is detected by a pressure sensor, with the first open/close valve being controlled to be turned on and off so that the accumulator maintains a pressure within a given range. Air of a positive pressure from the positive pressure accumulator is supplied to an artificial heart through a second positive pressure open/close valve by opening the latter during the systole of the artificial heart. On the other hand, a negative pressure from a decompressor (vacuum suction unit) is applied through a first negative pressure open/close valve to a negative pressure accumulator, the pressure of which is also detected by a pressure sensor, with the first open/close valve being controlled to be turned on and off, so that the negative pressure accumulator maintains a pressure within a given range. The negative pressure from the negative pressure accumulator is applied to the artificial heart through a second negative pressure open/close (O/C) valve by opening the latter during the diastole of the artificial heart.

The positive and the negative pressure alternately applied to the artificial heart are substantially equal to the pressures which prevail in the positive and the negative pressure accumulator, respectively. In this manner, the first positive pressure and negative pressure valves in combination with the positive pressure and the negative pressure sensor are effective to determine the magnitude of the positive pressure and the negative pressure which are effective to drive the artificial heart for contraction and expansion, respectively, while the second positive pressure and negative pressure valves are effective to switch between the positive and the negative pressure as fed to the artificial heart.

It will be appreciated that when either accumulator has an increased capacity, the magnitude of a reduction in the internal pressure of that accumulator when the second valve is changed from its closed to its open condition remains low, and a variation in the magnitude of a pressure supplied to the artificial heart which is caused by the opening and closing of the first valves also remains small. If the capacity of the accumulator is reduced or the provision of such accumulator is omitted, there occurs an overhunting of an increased magnitude when the pressure supplied to the artificial heart rises to a given value in response to a switching of the second valve from its closed to its open condition, and there also occurs a greater variation in the magnitude of pressure supplied to the artificial heart which occurs in response to the opening and closing of the first valve for pressure regulating purposes. In consideration of these aspects, the cited U.S. Patent chooses a capacity of the accumulator on the order of 4,000 cc, for example, so that the overhunting of the pressure supplied to the artificial heart in response to a change of the second valve from its closed to its open condition as well as a variation in the pressure supplied to the artificial heart in response to the opening/closing of the first valve be maintained small. If the capacity of the accumulator is reduced to the order of 300 cc or less, there occurs a variation in the pressure supplied to the artificial heart during the systole and the diastole which is excessively high.

It will be noted that in the arrangement mentioned above, a positive pressure drive system requires a first and a second open/close valve and a negative pressure drive system also requires a first and a second negative pressure open/close valve, thus requiring an increased number of valve units. The provision of the second valves is essential in order to achieve the pumping operation, and it may be noted that the first valves may be omitted by providing accumulators of sufficient capacity and providing a constant torque control of the compressor and the decompressor or adding a constant pressure relief valve. However, there may be experienced a difficulty in regulating the driving pressure, in particular, in achieving a pressure regulation of a relatively small magnitude.

SUMMARY OF THE INVENTION

It is a first object of the invention to provide a pumping drive unit which produces a reduced variation in the pressure supplied to a pumping unit and which is capable of reducing the capacity of or substantially eliminating accumulators.

It is a second object of the invention to provide a pumping drive unit which enables a pressure regulation while reducing the number of valve units used and reducing the capacity of accumulators.

The both objects mentioned above are achieved by a first embodiment of the invention comprising pressure detecting means for detecting a fluid pressure which prevails in a fluid space extending from a positive pressure open/close valve unit and a negative pressure open/close valve unit, which operate to supply a positive and a negative pressure from a positive pressure accumulator and a negative pressure accumulator, respectively, to a pumping unit, to a drive chamber of the pumping unit; and drive pressure control means operative during a preset systole of the pumping unit to close the positive pressure O/C valve unit in response to a pressure detected by the pressure detecting means which is equal to or greater than a first value and to open the positive pressure O/C valve unit when the detected pressure is less than the first given value and operative during a preset diastole of the pumping unit to close the negative pressure O/C valve unit in response to a pressure detected by the pressure detecting means which is equal to or less than a second given value and to open the negative pressure O/C valve unit when the detected pressure exceeds the second given value.

In the operation of the first embodiment, during the systole, the positive pressure O/C valve unit is opened to apply a pressure from the positive pressure accumulator to the pumping unit. The pressure supplied to the pumping unit is detected by the pressure detecting means. If the pressure detected by the detecting means is equal to or greater than the first given value (a positive pressure), the drive pressure control means closes the positive pressure O/C valve unit, and opens the positive pressure O/C valve unit if the detected pressure is less than the first given value. In this manner, the positive pressure O/C valve unit is opened and closed to feed a constant pressure or so that the positive pressure supplied to the pumping unit assumes the first given value.

During the diastole, the negative pressure O/C valve unit is opened to apply a pressure from the negative pressure accumulator to the pumping unit. The pressure supplied to the pumping unit is detected by the pressure detecting means. If the detected pressure is equal to or less than the second given value (a negative pressure), (more negative) the drive pressure control means closes the negative pressure O/C valve unit, and opens it if the detected pressure exceeds the second given value. In this manner, the negative pressure O/C valve unit is opened and closed to feed a constant pressure or so that the negative pressure supplied to the pumping unit assumes the second given value.

In this manner, the provision of the first positive pressure and the first negative pressure open/close valve which have been used in the prior art for pressure regulating purposes can be dispensed with. If the capacity of the positive and the negative pressure accumulator is reduced, a given pressure can be supplied to the pumping unit by maintaining the absolute magnitude of the pressure from these accumulators relatively high with respect to the driving pressure used in the pumping unit.

The both objects mentioned above can also be accomplished by a second embodiment of the invention comprising a positive pressure open/close valve unit interposed between a source of positive pressure fluid and a drive chamber of a pumping unit; a negative pressure open/close valve unit interposed between a source of negative pressure and the drive chamber, pressure detecting means for detecting a fluid pressure in a fluid space extending from the both valve units to the drive chamber; and pressure regulating control means operative during a preset systole of the pumping unit to maintain the positive pressure O/C valve unit open as long as the pressure detected by the pressure detecting means remains equal to or less than a first given value and to operate the positive pressure O/C valve unit with a given duty cycle when the detected pressure exceeds the first given value and also operative during a preset diastole of the pumping unit to maintain the negative pressure O/C valve unit open as long as the pressure detected by the pressure detecting means is equal to or greater than a second given value which is less than the first given value and to operate the negative pressure O/C valve unit with a given duty cycle when the detected pressure is less than the second given value.

In the operation of the second embodiment, during the systole, the positive pressure O/C valve unit is opened to apply a pressure from a positive pressure accumulator (or if such accumulator is not provided, from a source of positive pressure) to the pumping unit. The pressure supplied to the pumping unit is detected by the pressure detecting means. The pressure control means maintains the positive pressure O/C valve unit open as long as the detected pressure remains equal to or less than the first ates the positive pressure O/C valve given value and operates the positive pressure O/C valve unit with a given duty cycle when the detected pressure exceeds the first given value. Accordingly, the positive pressure O/C valve unit is maintained open to permit the pressure supplied to the drive chamber to be increased rapidly when the positive pressure O/C valve unit is opened while the negative pressure O/C valve unit is closed during the systole until the pressure of the drive chamber reaches the first given value. When the pressure reaches the first given value, the positive pressure O/C valve unit is operated with a given duty cycle, providing a moderate pressure rise, thus preventing an overhunting of positive pressure from occurring.

During the diastole, the positive pressure O/C valve unit is closed while the negative pressure O/C valve unit is opened to apply a pressure from a negative pressure accumulator (or if such accumulator is not provided, from a source of negative pressure) to the pumping unit. Again, the pressure supplied to the pumping unit is detected by the pressure detecting means. The pressure regulating control means maintains the negative pressure O/C valve unit open as long as the detected pressure remains equal to or greater than the second given value, and operates the negative pressure O/C valve unit with a given duty cycle when the pressure reduces below the second given value. Accordingly, the negative pressure O/C valve unit is maintained open to permit the pressure supplied to the drive chamber to be reduced rapidly when the negative pressure O/C valve unit is opened while the positive pressure O/C valve unit is closed during the diastole when the pressure of the drive chamber is reduced to the second given value. When the pressure reaches the second given value, the negative pressure O/C valve unit is operated with a given duty cycle to provide a moderate pressure fall, thus preventing an overhunting of a negative pressure from occurring.

Accordingly, the first positive pressure and negative pressure O/C valves which have been used in the prior art for pressure regulating purposes can be dispensed with. The positive and the negative pressure accumulators may be of a reduced capacity or omitted, but still a given pressure can be supplied to the pumping unit by maintaining the absolute magnitude of the pressure of the accumulators (or sources) relatively high with respect to the driving pressure for the pumping unit.

The first object mentioned above can also be accomplished by a third embodiment of the invention comprising a positive pressure open/close valve unit for supplying a fluid of positive pressure to a pumping unit; a positive pressure regulator valve unit disposed between a source of fluid of positive pressure and the positive pressure O/C valve unit for opening or closing a fluid path therebetween to regulate a fluid pressure supplied to the positive pressure O/C valve unit from the source; first pressure detecting means for detecting a fluid pressure which prevails between the first pressure regulator valve unit and the positive pressure O/C valve unit; a negative pressure open/close valve unit for supplying a negative pressure to the pumping unit; a negative pressure regulator valve unit interposed between a source of negative pressure and the negative pressure O/C valve unit to open or close a fluid path therebetween to regulate a negative pressure supplied to the negative pressure O/C valve unit from the source of negative pressure; second pressure detecting means for detecting a fluid pressure which prevails between the negative pressure regulator valve unit and the negative pressure O/C valve unit; pressure regulating control means operative to maintain the positive pressure regulator valve unit open as long as the pressure detected by the first pressure detecting means remains equal to or less than a first given value and to operate the positive pressure regulator valve unit with a given duty cycle when the pressure exceeds the first given value and also operative to maintain the negative pressure regulator valve unit open as long as the pressure detected by the second pressure detecting means remains equal to or greater than a second given value which is less than the first given value and to operate the negative pressure regulator valve unit with a given duty cycle when the pressure reduces below the second given value; and pressure switching control means operative during a preset systole of the pumping unit to open the positive pressure O/C valve unit and to close the negative pressure O/C valve unit and also operative during a diastole to close the positive pressure O/C valve unit and to open the negative pressure O/C valve unit.

In the operation of the third embodiment, during the systole, the pressure switching control means opens the positive pressure O/C valve unit and closes the negative pressure O/C valve unit, whereby a positive pressure is supplied to the drive chamber of the pumping unit. Conversely, during the diastole, the pressure switching control means closes the positive pressure O/C valve unit and opens the negative pressure O/C valve unit, whereby a negative pressure is supplied to the drive chamber of the pumping unit. It will be noted that such operation takes place in the similar manner as in the prior art. Components used also remain similar as those used in the prior art, except for the following differences.

When the pressure from a positive pressure accumulator (or a corresponding location if such accumulator is absent) remains equal to or less than the first given value, the pressure regulating control means maintains the positive pressure regulator valve unit open, and operates it with a given duty cycle when the pressure exceeds the first given value. Accordingly, when the positive pressure O/C valve unit is changed from its closed to its open condition to cause a rapid reduction in the pressure from the positive pressure accumulator, the pressure of the positive pressure accumulator can be rapidly returned to its normal value without accompanying an overshoot. When the pressure from the negative pressure accumulator (or a corresponding location if such accumulator is absent) remains equal to or greater than the second given value, the pressure regulating control means maintains the negative pressure regulator valve unit open and to operate it with a given duty cycle when the pressure reduces below the second given value. Accordingly, when the pressure of the negative accumulator rapidly increases (meaning a reduction in the negative pressure) as a result of switching the negative pressure O/C valve unit from its closed to its open condition, the negative pressure accumulator can be rapidly returned to its normal negative pressure, again without accompanying an overshoot.

Accordingly, the positive and the negative accumulator may be of a reduced capacity or may be dispensed with, but a given pressure can still be supplied to the pumping unit by maintaining the absolute magnitude of pressure of these accumulators (or sources of pressure) relatively high with respect to the driving pressure for the pumping unit.

Other objects and features of the invention will become apparent from the following description of several embodiments thereof with reference to the drawings.

DESCRIPTION OF PREFERRED EMBODIMENT

First Embodiment

Figure 1:
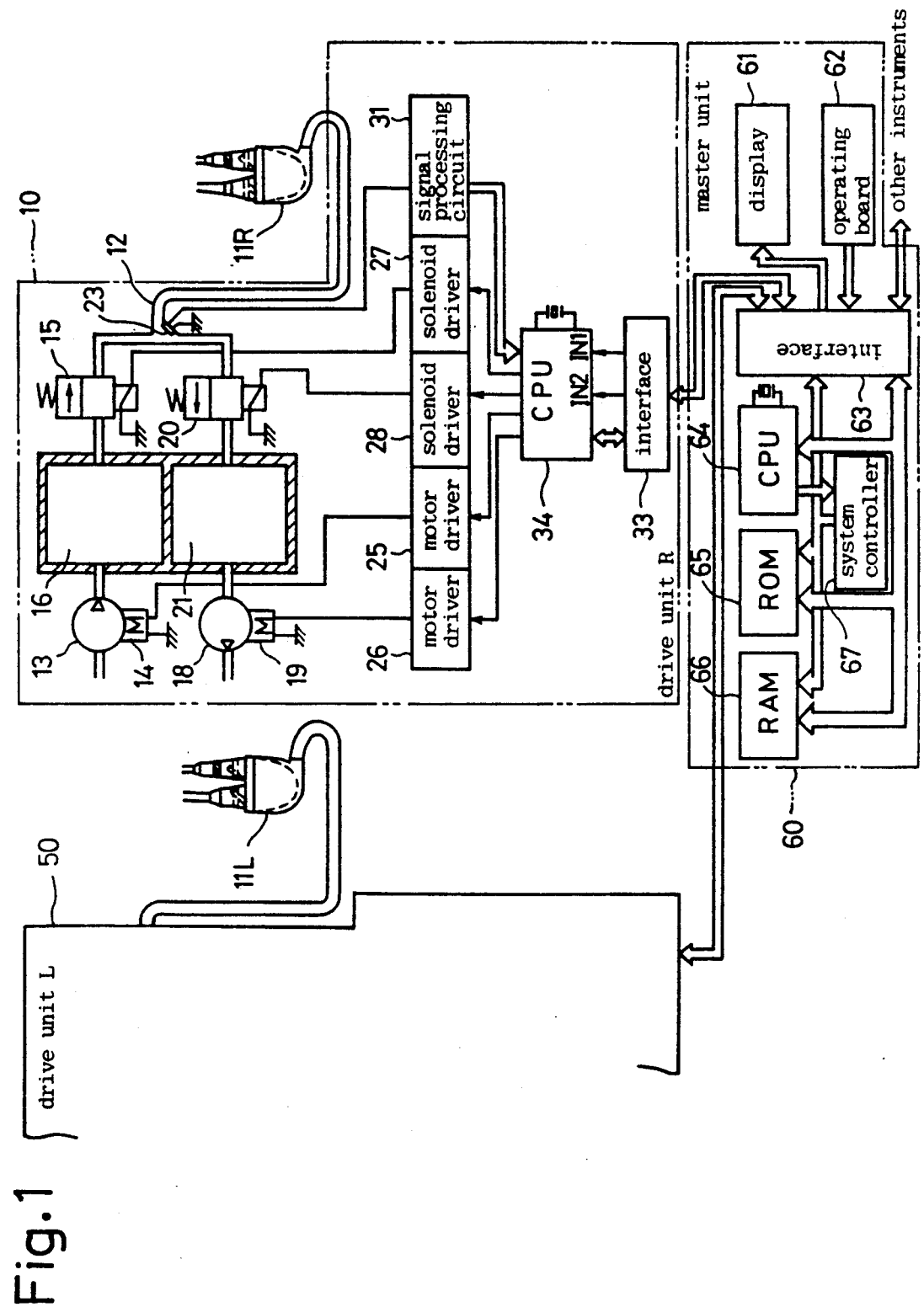
FIG. 1 is a block diagram of a first embodiment of the invention.

FIG. 1 shows one embodiment of the invention, which is constructed as an artificial heart driving apparatus. A right-hand artificial heart 11R and a left-hand artificial heart 11L are constructed by flexible diaphragms which form partitions between a suction chamber which draws blood of a living body and a drive chamber into which a driving air is introduced. The suction chamber is connected to a blood drawing piping with a check valve interposed therebetween, which permits a fluid flow from the piping to the chamber, but blocks a reverse flow. The suction chamber is also connected to a blood discharge piping with another check valve interposed therebetween, which is effective to permit a flow from the chamber to the piping, but blocks a reverse flow. When air of an increased pressure is supplied to the drive chamber, the flexible diaphragm compresses the suction chamber, whereby a fluid within the suction chamber flows out through the blood discharge piping. When a negative pressure is introduced into the drive chamber, the flexible diaphragm allows the suction chamber to expand, thus drawing fluid from the blood drawing piping into the suction chamber. In this manner, by alternately supplying air of a positive pressure and a negative pressure to the drive chamber, the artificial heart is effective to draw fluid (blood) from the drawing piping and to deliver the fluid through the discharge piping.

The drive chamber of the artificial heart 11R is connected through a tube 12 to an output port of a positive pressure open/close valve 15 and an input port of a negative pressure open/close valve 20 (or an output port thereof for a negative pressure). A pressure sensor 23 is disposed to detect a pressure or driving pressure which prevails in an air path communicating with the drive chamber of the heart 11R.

The positive pressure O/C valve 15 has an input port which communicates with a positive pressure accumulator 16, and the negative O/C pressure valve 20 includes an input port which communicates with a negative pressure accumulator 21. An air compressor 13 which is driven by a d.c. motor 14 supplies compressed air to the accumulator 16 while a decompressor (vaccum suction unit) 18 which is driven by another d.c. motor 19 draws air from the accumulator 21. It is to be understood that the discharge pressure from the air compressor 13 is higher than a range of positive pressures (a level c shown in FIG. 5b) required by the heart 11R while the absolute magnitude of the suction produced by the decompressor 18 is lower than a range of negative pressures (a level h shown in FIG. 5b) required by the heart 11R.

The valves 15 and 20 are similar to solenoid valves which are specifically disclosed in cited U.S. Pat. No. 4,546,760. Specifically, each valve is opened to pass a fluid flow when its associated electrical coil is energized, and is closed to interrupt a fluid flow when the coil is deenergized.

The pressure sensor 23 is connected to a signal processing circuit 31, which comprises an A/D converter (including a combination of a comparator and an encoder) effective to convert an analog pressure signal from the sensor 23 into a corresponding digital data, an output latch, and a timing circuit which activates the output latch for updating purposes with a preselected short period and which also delivers a latch command pulse to a microprocessor (hereafter referred to as CPU) 34. The output latch normally feeds digital data to CPU 34.

Solenoid drivers 27 and 28 are constructed in a known manner, and when a high level H is applied thereto from CPU 34, each of them is effective to energize the electrical coil of either solenoid valve 15 or 20 to open the respective valves.

Motor drivers 25 and 26 each include a potentiometer which allows the magnitude of a drive torque to be adjusted. When a high level H is applied to either motor driver from CPU 34, it energizes the corresponding motor 14 or 19 with a current of a magnitude which is determined by the position of the potentiometer for producing a given torque. It will be noted that CPU 34 is connected to a master unit 60 through an interface 33.

It will be understood that a remedy of hearts normally requires a pair of artificial hearts for a single patient to assist in the operation of or substitute for the function of his hearts. Accordingly, a drive unit 10 associated with a right-hand artificial heart (11R) and another drive unit 50 associated with a left-hand artificial heart (11L) and having the same construction as the drive unit 10 are both connected to the master unit 60.

It will be noted that the master unit 60 essentially comprises a computer system including a display unit 61 including a character display, indicator lamps and buzzers, an operating board 62, an interface 63, CPU 64, ROM 65, RAM 66 and a system controller 67. CPU 64 is connected with a cardiograph and other medical instruments which detect or monitor the status of various organs of a patient in which the artificial hearts 11R and 11L are incorporated, through the interface 63. Based on drive pressures (R-positive pressure, L-positive pressure, R-negative pressure and L-negative pressure) fed from the operating board 62, R-ratio (the ratio of the systol to the diastole of the right-hand artificial heart), L-ratio (the ratio of the systole to the diastole of the left-hand artificial heart) and the heart rate (the number of heartbeats per minute, required when the cardiograph is not connected) or a cardiographic pulse from the cardiograph, CPU 64 of the master unit 60 calculates the timing to initiate the systole and the diastole (or to end the diastole or the systole, respectively) for the right-hand and the left-hand artificial hearts 11R and 11L, respectively. A pulse (IN1 interrupt pulse) representing the timing to initiate the systole and a pulse (IN2 interrupt pulse) representing the timing to initiate the diastole are developed for each of R and L hearts, and are delivered to the drive units 10 and 50 associated therewith. R-positive pressure (a first given value for R) and R-negative pressure (a second given value for R) are transmitted to the drive unit 10 while L-positive pressure (a first given value for L) and L-negative pressure (a second given value for L) are transmitted to the drive unit 50. Such transmission takes place upon entry from the operating board 62.

Figure 2A:
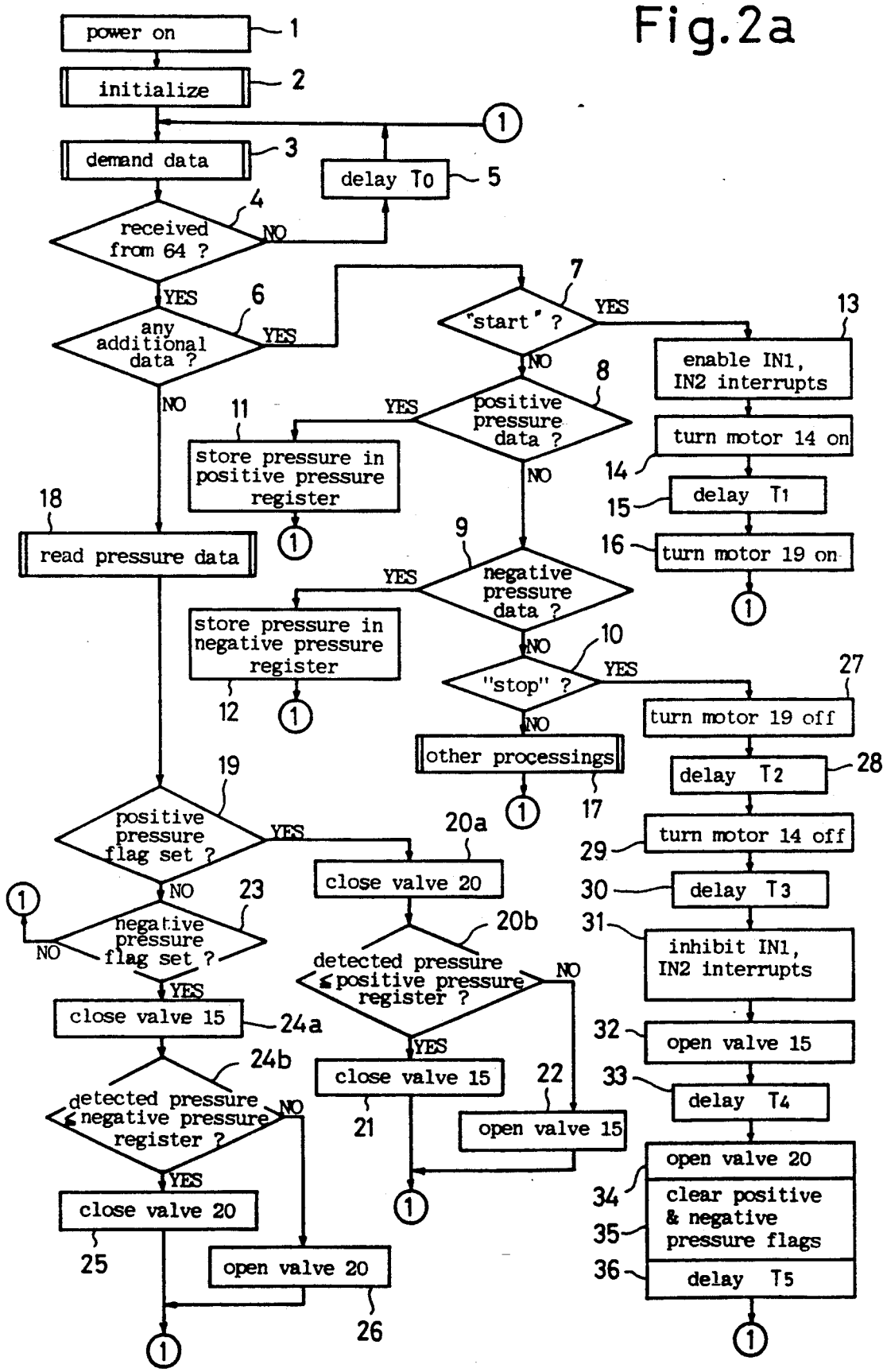
FIG. 2a is a flowchart of a control operation by CPU 34 shown in FIG. 1.
Figure 2B:
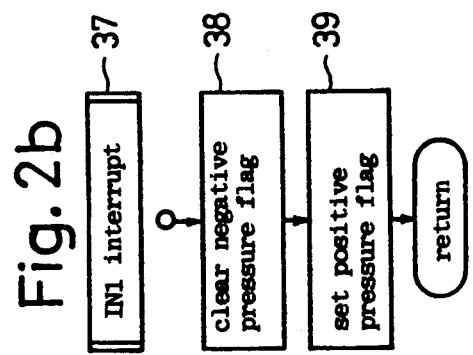
FIGS. 2b and 2c are flowcharts illustrating an interrupt processing operation by CPU 34.
Figure 2C:
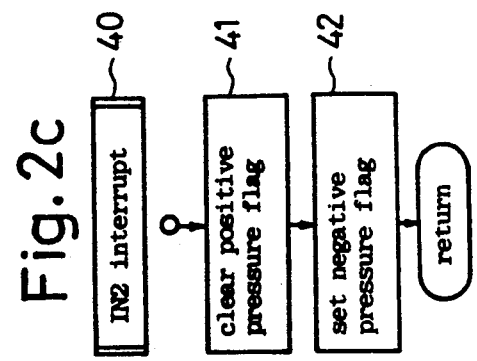
Figure 3:
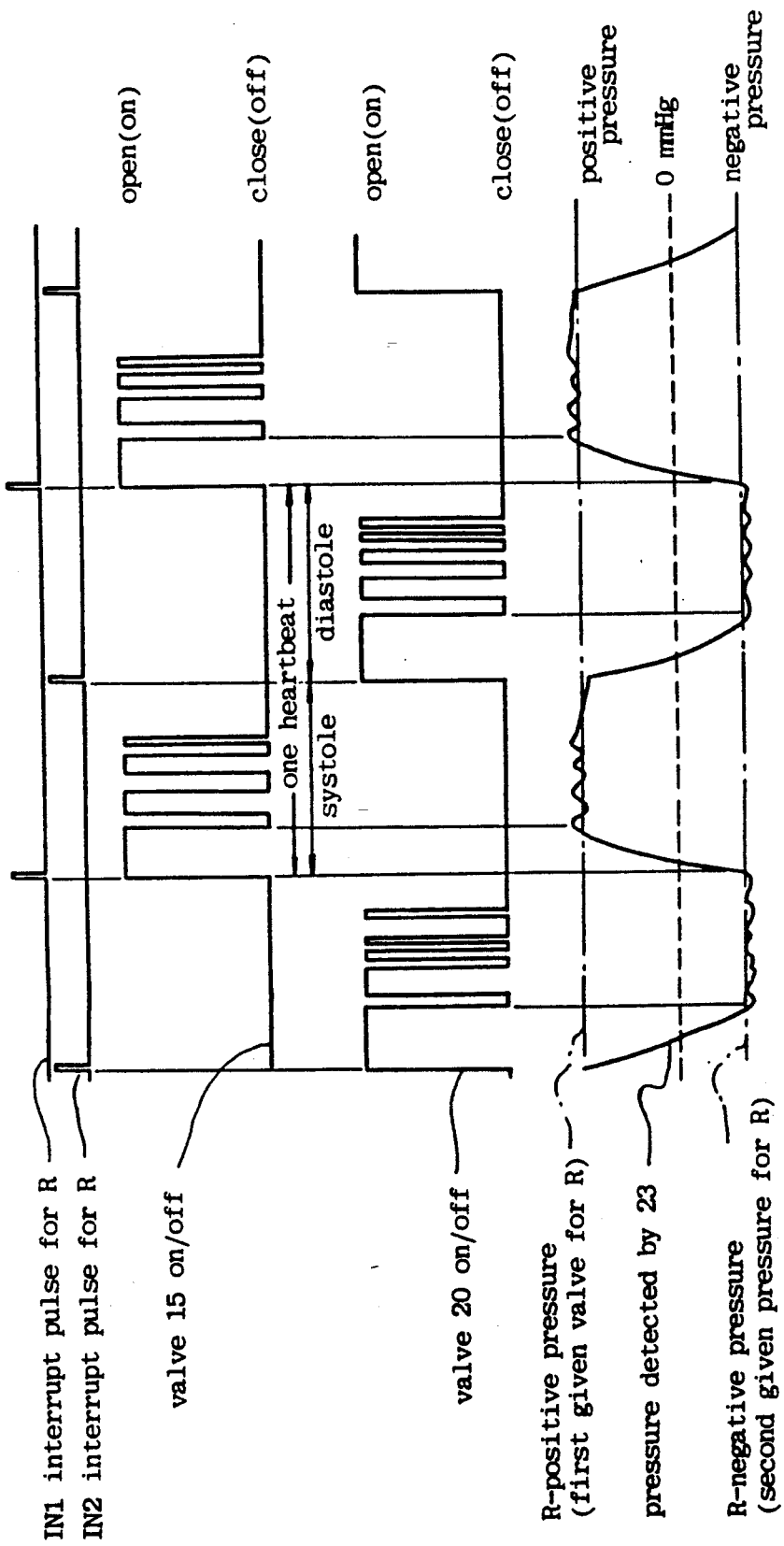
FIG. 3 graphically shows a series of timing charts illustrating the relationship between the opening and closing of solenoid valves 15, 20 shown in FIG. 1 and a pressure applied to an artificial heart 11R shown in FIG. 1.

FIG. 2a shows a control operation by CPU 34 of the drive unit 10 associated with the right-hand artificial heart 11R. FIGS. 2b and 2c show interrupt operations responsive to the timing pulses, namely, IN1 and IN2 interrupt pulses for R.

Initially referring to FIG. 2a, when the power is turned on at step 1 (in the subsequent description, it is to be noted that a step number is indicated by a number appearing in parentheses), CPU 34 presets the signals at its input and output ports to their standby or off condition (16, 20, 14, 18), clears internal timers, counters, registers and flags, and inhibit IN1 and IN2 interrupts (2). CPU 34 then demands CPU 64 to supply data (3).

The data transfer between CPU 34 and CPU 64 takes place in the form of a frame comprising start bits, data bits, end bits and error check bits, and when demanding data at step 3, CPU 34 places "ready" in the "data" term of this frame. When CPU 64 receives one frame from CPU 34, it places any data which is then to be transmitted to CPU 34 into the "data" term of one frame for transmission to CPU 34. When it has no data to be transmitted (meaning that the current status is to be continued), CPU 64 places "ACK" (acknowledge) into the "data" term of the frame which is to be transmitted.

Upon issuing data demand to CPU 64 (3), CPU 34 sets up a timer T₀ (program timer) and waits for its timeout (5). If it receives a transmission from CPU 64 before the time-out, the program proceeds to step 6. When there is no transmission, it transmits another frame to CPU 64.

Subsequent operation of CPU 34 and CPU 64 will be described in a manner corresponding to a key operation of an operator on the operating board 62.

I. When an operator enters R-positive pressure on the operating board 62, CPU 64 transmits it to CPU 34, which in response proceeds through steps 4, 6, 7, 8 and 11 where it stores it in a positive pressure register (an internal register of CPU 34). L-positive pressure is also set up in the drive unit 50 in a similar manner.

II. When an operator enters R-negative pressure on the operating board 62, CPU 64 transmits it to CPU 34 which in response proceeds through steps 4, 6, 7, 8, 9 and 12 where it stores it in a negative pressure register (an internal register of CPU 34). L-negative pressure is set up in the drive unit 50 in a similar manner.

III. When a cardiograph is not connected to the arrangement of the invention, CPU 64 calculates the period of one heartbeat Th, the period of R-systole Trc and the period of L-systole Tlc on the basis of R-ratio, L-ratio and the heart rate which are entered through the operating board 62. A pulse having the period Th (representing IN1 interrupt pulse for R) is developed by a timer controlled operation and is delivered to IN1 interrupt port of CPU 34. Another pulse (IN2 interrupt pulse for R) is developed with a time delay of Trc from the IN1 interrupt pulse for R, and is delivered to IN2 interrupt port of CPU 34. On the basis of phase displacement data representing a phase displacement of L relative to R which is input from the operating board 62, CPU 64 calculates a phase displacement Tpd of L relative to R, and the pulse 9IN1 interrupt pulse for L) is displaced so as to be phase displaced by Tpd with respect to IN1 interrupt pulse for R, and is delivered to the drive unit 50. Another pulse (IN2 interrupt pulse for L) which is delayed by Tlc with respect to IN1 interrupt pulse for L is developed and delivered to the drive unit 50. The process of generating these pulses extends from a point in time immediately preceding a "start" command until immediately after such command, which is applied to the drive units 10 and 50. When there is an updated input from the operating board 42 during such process, the described calculations are performed again to update the timing to generate these pulses.

Where a cardiograph is employed, CPU 64 develops IN1 interrupt pulse for R as a cardiographic wave (pulse) occurring with the period of the heartbeat delayed by a time delay which is inputted from the operatingt board 62. Other pulses are developed in the manner mentioned above as referenced to the IN1 interrupt pulse.

IV. When "start" is entered on the operating board 62 and CPU 64 responds thereto by transmitting "start" command to CPU 34, the latter proceeds through steps 4, 6, 7 and 13, enabling IN1 and IN2 interrupts (13), delivering a command signal which causes the energization of the compressor motor 14 to the motor driver 25, by establishing a corresponding level at its associated port (14) and waiting for the time duration $T_1$ to pass during which a transient high current due to the starting of the motor prevails (15) before delivering a command signal which causes an energization of the decompressor motor 19 to the motor driver 26 (16). The program then proceeds to a demand for data (3). CPU 64 similarly supplies "start" command to the drive unit 50, whereupon a microprocessor (not shown) of the drive unit 50 operates in the similar manner as CPU 34 described above.

Since the interrupt operation is enabled at step 13, in response to IN1 interrupt pulse for R delivered to the interrupt port IN1 of CPU 34 and to IN2 interrupt pulse for R delivered to the interrupt port IN2 of CPU 34, both from CPU 64, CPU 34 executes an IN1 interrupt subroutine (37) shown in FIG. 2b in response to IN1 interrupt pulse or executes an IN2 interrupt subroutine (40) shown in FIG. 2c in response to IN2 interrupt pulse for R. These subroutines are executed until step 31 where IN1 and IN2 interrupts are inhibited.

In response to IN1 interrupt pulse for R, CPU 34 proceeds to the IN1 interrupt subroutine (34) shown in FIG. 2b where it clears a negative pressure flag (data indicating the systole) (38) and sets a positive pressure flag (data representing the diastole) (39). The program then returns to the main routine shown in FIG. 2a at a point which immediately precedes the interrupt subroutine (37).

In response to IN2 interrupt pulse for R, CPU 34 enters the IN1 interrupt subroutine (40) shown in FIG. 2c where it clears a positive pressure flag (41) and sets a negative pressure flag (42). The program then returns to the main routine at a point which immediately precedes the interrupt subroutine (40).

CPU 64 delivers IN1 interrupt pulse for L and IN2 interrupt pulse for L to the drive unit 50 also, the microprocessor of which executes an interrupt operation in a similar manner as mentioned above in connection with CPU 34 (see FIGS. 2b and 2c). CPU of the drive unit 50 operates in the same manner as CPU 34, and the drive unit 50 is arranged and operates in the similar manner as the drive unit 10, and therefore will not be described. Thus, the ensuing description covers only the drive unit 10.

V. Returning to FIG. 2a, when the compressor 14 and the decompressor 19 are energized in response to the "start" command as mentioned previously, CPU 34 executes data demand (3), receives one frame of data from CPU 64 (4) and then proceeds to step 6 where it is examined if there is any additional parameter data. Unless updated input, representing a change in the operating parameters, is input from the operating board 62, the data in the frame represents "ACK" and includes no fresh data. Accordingly the program proceeds to step 18 where CPU 64 reads an output or pressure data from the signal processing circuit 31. The circuit 31 includes an internal output latch which is updated with a given short period, by applying a latch pulse to the output latch. This latch pulse is applied to CPU 34. Output data from the circuit 31 exhibits a degraded reliability during a pulse interval, which may be at H level, for example, of the latch pulse, and hence when CPU 34 proceeds to the step 18 of reading pressure data during such pulse interval (H), it waits for this pulse interval to pass or until the latch pulse is removed or assumes an L level, whereupon CPU 64 reads output data from the circuit 31. After passing through the step 18, CPU 34 executes a "pressure control" comprising steps 19 to 26, after which the program returns to the data demand step 3.

Unless fresh input is supplied from the operating board 62, CPU 64 does not transmit parameter data while transmitting only "ACK" in response to the data demand at step 3. Accordingly, CPU 34 loops around the steps 3, 4, 6, 18, 19 to 26 and 3, thus in effect repeating a reading of pressure data at step 18 and the "pressure control" comprising steps 19 to 26 with a fixed period.

VI. During the "pressure control" comprising steps 19 to 26, it is initially examined if either the positive or the negative flag is set (19, 23). If neither flag is set, this means that the "start" command has not been issued, and hence the program returns to the step 3. The "pressure control" is not executed in effect.

However, when the positive pressure flag is set, as by the IN1 interrupt subroutine (37) shown in FIG. 2b, this signifies that it is now in the systole, thus midway from the occurrence of IN1 interrupt pulse to the occurrence of IN2 interrupt pulse. At this time, the solenoid valve 20 is turned off to close its associated valve (20a), and pressure data or detected pressure which is obtained at the step 18 of reading the pressure data is compared against the content of the positive pressure register (a first given value: corresponding to an R-positive pressure which has previously been input from the operating board 62 and supplied through CPU 64) (20b). If the detected pressure is equal to or greater than the first given value, the solenoid valve 15 is turned off to close the valve. If the detected pressure is less than the first given value, the solenoid valve 15 is turned on to open the valve in order to compensate for a reduced pressure.

When the negative pressure flag is set, at the IN2 interrupt subroutine (40) of FIG. 2c, this signifies that it is now in the diastole, namely, midway from the occurrence of IN2 interrupt pulse to the occurrence of IN1 interrupt pulse. At this time, the solenoid valve 15 is turned off (24a), and pressure data or detected pressure which is obtained at the step 18 of reading the pressure data is compared against the content of the negative pressure register (a second given value: corresponding to R-negative pressure which has previously been input from the operating board 62 and fed through CPU 64) (24b). If the detected pressure is equal to or less than the second given value, the negative pressure has an excessively high absolute magnitude, and accordingly, the solenoid valve 20 is turned off. If the detected pressure exceeds the second given value, meaning a small absolute magnitude of the negative pressure, the solenoid valve 20 is turned on.

As a result of the pressure control mentioned above, the solenoid valve 20 remains closed while the solenoid valve 15 is opened and closed to achieve a pressure detected by the sensor 23 which is equal to the first given value during the systole when the positive pressure flag is set. On the other hand, during the diastole when the negative pressure flag is set, the solenoid valve 15 remains closed while the solenoid valve 20 is opened and closed to achieve a pressure detected by the sensor 23 which is equal to the second given value. In this manner, by providing a single solenoid valve 15 or 20 in each of the positive and the negative pressure system, an alternate switching between the positive and the negative pressure is achieved together with a constant positive and negative pressure control.

VII. When there is an input from the operating board 62 during the execution of the pressure control or while the artificial heart 11R is being driven, the operation takes place in a similar manner as described above under paragraphs I and II. Specifically, CPU 64 transmits data to CPU 34, which updates the content of the registers by the received data. CPU 64 re-calculates the timing, thus modifying the interrupt pulses so as to be based upon the re-calculated data. Accordingly, the pressure control mentioned above under paragraph VI changes to one which is based upon the data and pulses thus modified.

VIII. When an operator enters a "stop" command on the operating board 62, CPU 64 transmits it to CPU 34. Upon receiving the "stop" command, CPU 34 proceeds through steps 4, 6, 7, 8, 9, 10 and 27, ceasing to drive the decompressor (27), waiting for the transient stop period $T_2$ to pass (28), ceasing to drive the compressor 14 (29), waiting for the transient stop period $T_3$ to pass (30), and inhibiting IN1 and IN2 interrupt operations (31). The artificial heart 11 ceases to operate since IN1 and IN2 interrupt subroutines (FIGS. 2b and 2c) are no longer executed to update the flags. CPU 34 then turns the solenoid valve 15 on (32), waits for a transient period $T_4$ associated with the energization of the coil to pass (33), and then turns the solenoid valve 20 on (34). As a result of turning the both solenoid valves 15 and 20 on, the compressed air from the positive pressure accumulator 16 flows into the negative pressure accumulator 21, whereby the pressure within the both accumulators 16 and 21 approach the atmospheric pressure. CPU 34 then clears both the positive and the negative pressure flag (35), and waits for a time period $T_5$ to pass which is sufficient to neutralize the pressures of both accumulators (36) before proceeding to the data demand step 3.

As mentioned, during the systole, the solenoid valve 15 is closed when the detected pressure is greater than the first given value (R-positive pressure) and is opened when the detected pressure is less than the first given value, thereby applying a pressure which is substantially equal to the first given value to the artificial heart 11. During the diastole, the solenoid valve 20 is closed when the absolute magnitude of the detected pressure is greater than the absolute magnitude of the second given value (R-negative pressure) and is opened when the detected pressure is less, thus applying a pressure which is substantially equal to the second given value to the artificial heart 11R. In this manner, the pressure of the accumulator 16 is chosen higher than the first given value while the absolute magnitude of the pressure of the negative pressure accumulator is chosen to be higher than the absolute magnitude of the second given value. It will be seen that the capacity of these accumulators may be reduced by an amount corresponding to the chosen higher pressures. Where the solenoid valves 15 and 20 exhibit rapid response, it is preferred to choose as high a pressure as possible of the accumulator in order to reduce the size of the accumulator. In such event, if it is required to provide a smooth rising or falling edge of the positive or negative pressure, a function generator such as an integrating circuit, ROM or RAM which provides a desired rising response may be used and activated in response to IN1 and IN2 interrupt pulses, and the solenoid valves 15 and 20 may be turned on and off as a result of a comparison of an output from the function generator against the pressure detected by the sensor 23.

It will be seen that according to the first embodiment of the invention, both a positive and a negative pressure system may include a single solenoid valve to produce a fluid of a given pressure during a specified interval, thus dispensing with pressure regulator valves required in the prior art practice and thus reducing the number of valves used. The capacity of the accumulators may also be reduced. In the prior art practice, a pressure sensor has been required for each pressure regulator valve, and hence two sensors must be provided. However, according to the invention, the number of pressure sensors required can be minimized to one.

Second Embodiment

Figure 4:
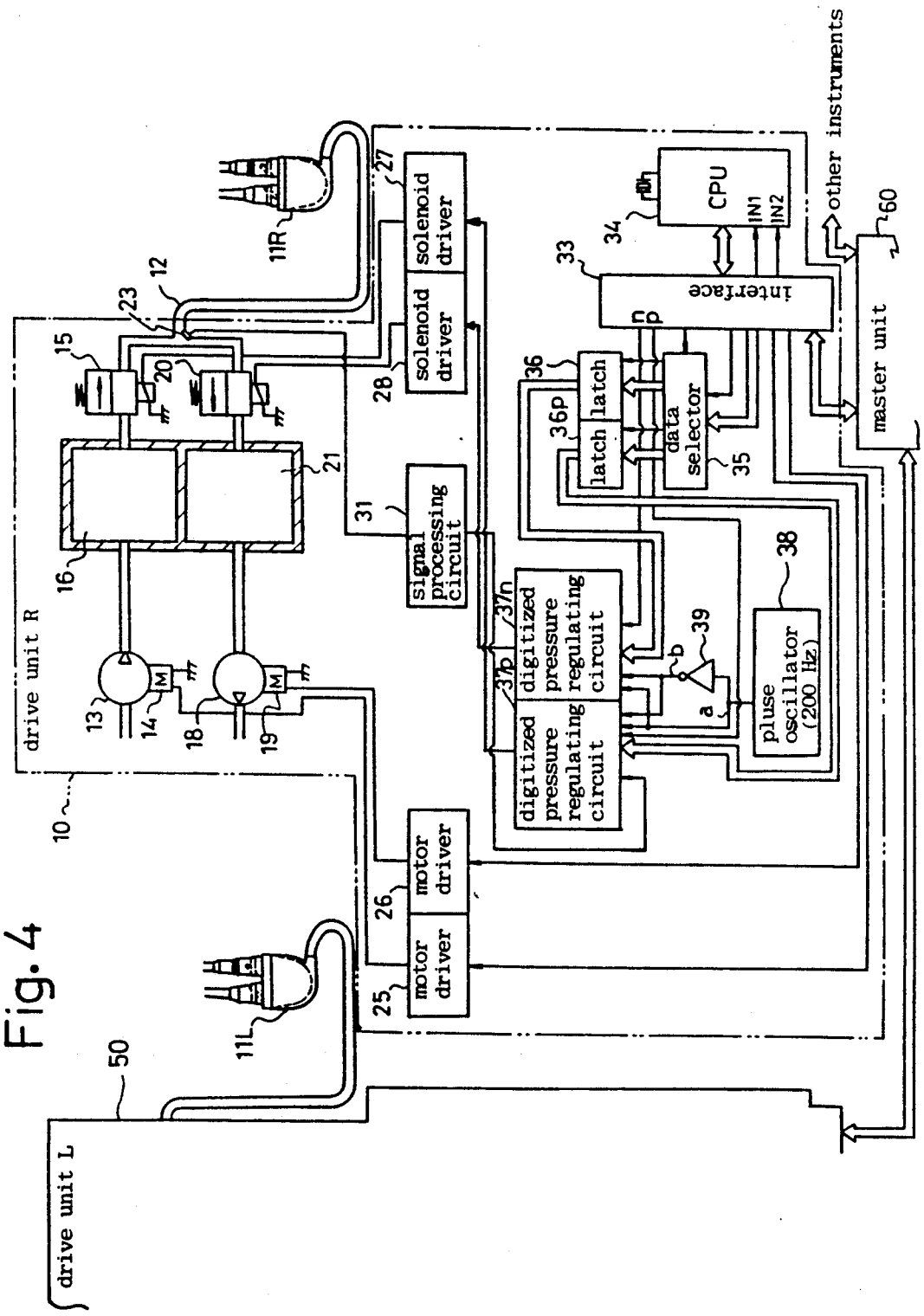
FIG. 4 is a block diagram of a second embodiment of the invention.

Referring to FIG. 4, the signal processing circuit 31 applies an analog signal representing a pressure detected by the sensor 23 to a pair of digitized pressure regulating circuits 37p and 37n. When a high level H is applied to solenoid drivers 27, 28 from the circuits 37p and 37n, respectively, the drivers energize the electrical coils associated with the solenoid valves 15 and 20, respectively, which are provided for opening to operate to supply or interrupt the positive and the negative pressure, respectively. When a low level L is applied to the drivers, the latter deenergizes the electrical coils to close the valves.

CPU 34 of the drive unit 10 responds to an R-positive pressure (a target value of R-positive pressure) from the master unit 60, by latching it in a latch 36p. Similarly, responsive to an R-negative pressure, a target value of R-negative pressure, CPU 34 latches it in a latch 36n.

CPU 34 of the drive unit 45 delivers a command signal having an H level which commands the valve 15 to open (thus representing a systole signal) to the digitized pressure regulating circuit 37p through an output port p of the interface 33 during a time from the reception of IN1 interrupt pulse to the reception of IN2 interrupt pulse from the master unit 60. It also delivers a command signal having an H level which commands the valve 20 to open (thus representing a diastole signal) to the digitized pressure regulating circuit 37n through an output port n of the interface 33 during the time interval from the reception of IN2 interrupt pulse to the reception of IN1 interrupt pulse from the master unit 60.

In addition to the command signal to open the valve 15 (systole signal), the digitized pressure regulating circuit 37p receives R-positive pressure data from a latch 36p, a pulse a having a duty cycle of 75% from a pulse oscillator 38 and a pulse b having a duty cycle of 25% from an inverter 39, which represents an inversion of the pulse a. In addition to the command signal to open the valve 20 (diastole signal), the digitized pressure regulating circuit 37p receives R-negative pressure data from a latch 36n, the pulse a from the pulse oscillator 38 and the pulse b from the inverter 39.

Figure 5A:
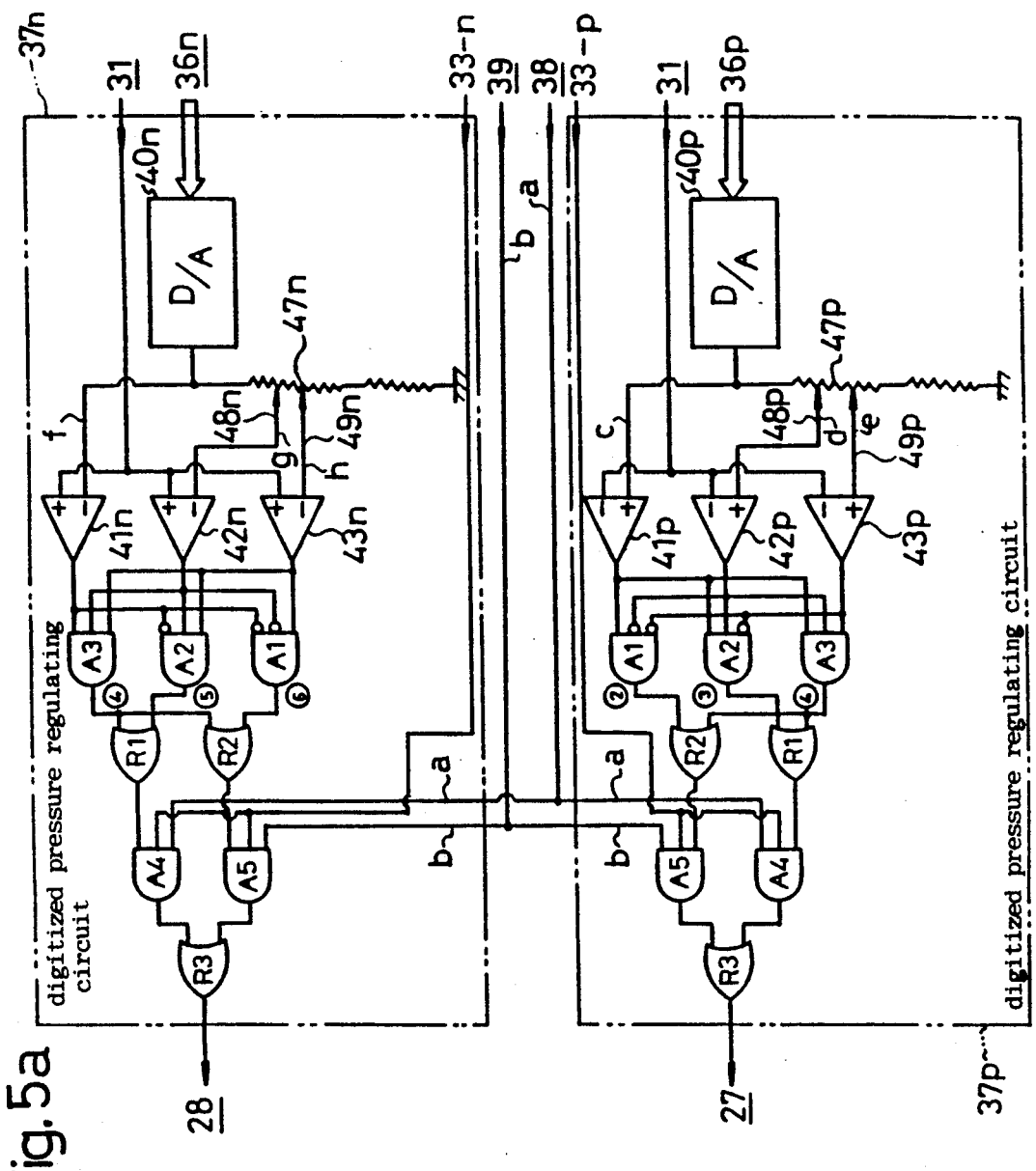
FIG. 5a is a block diagram of digitized pressure regulating circuits 37p and 37n shown in FIG. 4.

The arrangement of each of the pressure regulating circuit 37p and 37a are illustrated in FIG. 5a. Initially considering the circuit 37p, R-positive pressure (a target value Prp of positive pressure) fed from the latch 36p is converted into an analog signal c having a level corresponding to 1.05 times Prp (see FIG. 5b) by a D/A converter 40p to be applied to an inverting input of a comparator 41p. The analog voltage c is divided into signals d = 1.0 Prp and e = 0.90 Prp (first given value) by means of a variable resistor 47p, which are applied to inverting inputs of comparators 42p and 43p. An analog signal representing the pressure detected by the sensor 23 is applied to non-inverting inputs of comparators 41p to 43p.

When the pressure detected by the sensor 23 is equal to or less than e = 0.90 Prp (region ④ shown in FIG. 5b) when CPU 34 is delivering the command signal to open the valve 15 (or systole signal: shown by "33-p" in FIG. 5b), all of the comparators 41p to 43p deliver outputs of a high level H, whereby only one, A3, of AND gates A1 to A3 provides an output of a high level H, which is applied through OR gates R1 and R2 to AND gates A4 and A5. The gates A4 and A5 feed the signals a and b to OR gate R3, which then provides a logical sum of the signals a and b, or an open (on) signal, having a high level continuously, to the solenoid driver 27. Accordingly, the solenoid valve 15 remains open continuously, rapidly increasing the pressure applied to the artificial heart 11R.

When the pressure detected by the sensor 23 exceeds the first given value e = 0.90 Prp (region ③ shown in FIG. 5b), the comparators 42p and 41p provide outputs of a high level while the comparator 43p provides an output of a low level, whereby only gate A2 provides an output of a high level H, thus enabling only the gate A4 to feed only the signal a to the solenoid driver 27. As mentioned previously, the signal a represents a pulse having a duty cycle of 75% and a frequency of 200 Hz which is developed by the pulse oscillator 38. Accordingly, the solenoid valve 15 is opened and closed in an oscillating manner at such frequency and with such duty cycle. This reduces the rate of supplying the positive pressure, whereby the positive pressure which is applied to the artificial heart 11R rises more gently.

When the pressure detected by the sensor 23 becomes equal to or exceeds the target value d = 1.00 Prp (region ② shown in FIG. 5b), only the comparator 41p provides an output of a high level H while the comparators 42p and 43p provide outputs of a low level L. Thus only the gate A1 provides an output of a high level H, disabling the gate A4 and enabling the gate A5. Consequently, the signal b having a frequency of 200 Hz and a duty cycle of 25% is delivered to the solenoid driver 27, causing the solenoid valve 15 to be opened and closed in an oscillating manner at such frequency and with such duty cycle. This represents an insufficient rate of supplying the positive pressure, whereby the positive pressure applied to the artificial heart 11R decreases gently. Consequently, the pressure detected enters the region ③, whereby the rate of supplying the positive pressure rises gently. In this manner, a control continues which alternates between the regions ③ and ②.

If the detected pressure becomes equal to or greater than c = 1.05 Prp (region ① shown in FIG. 5b), all of the gates A1 to A3 provide outputs of a low level L, disabling the both gates A4 and A5, whereby the valve 15 remains closed, returning the pressure to the region ② rapidly.

The digitized pressure regulating circuit 37n is constructed in the similar manner as the circuit 37p mentioned above. When the pressure detected is equal to or greater than the second given value f = 1.05 Prn (region ④ shown in FIG. 5b) when CPU 34 is delivering the command signal to open the valve 20 (diastole signal: shown at "33-n" in FIG. 5b), it maintains the solenoid valve 20 open in order to reduce the pressure rapidly. When the detected pressure is less than f = 1.05 Prn and is equal to or greater than R-negative pressure (the target value of negative pressure) g = 1.00 Prn (region ⑤ shown in FIG. 5b), it applies the signal a to the solenoid driver 18 in order to reduce the pressure gently. When the detected pressure reduces below g = 1.00 Prn, it applies the signal b to the solenoid driver 28 in order to raise the pressure gently. If the detected pressure becomes equal to or less than h = 0.95 Prn, it applies a signal L to the solenoid driver 28 which commands the valve 20 to be closed in order to raise the pressure rapidly.

Figures 5B, 5C:
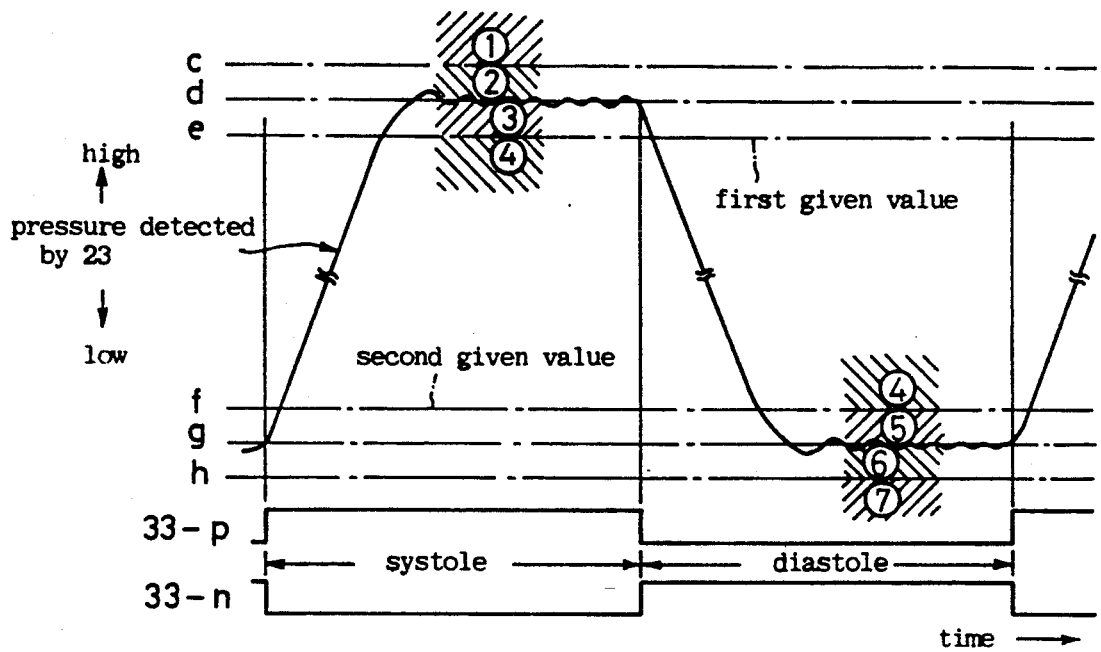
FIG. 5b graphically shows a pressure detected by a pressure sensor 23 shown in FIG. 4.
FIG. 5c is a chart illustrating the waveforms of output signals from the pressure regulating circuits 37p and 37n.

The upper half of the table shown in FIG. 5c indicates valve energizing signals applied by the circuit 37p to the solenoid driver 27 in a manner corresponding to the pressure detected by the sensor 23 (regions ① to ④ shown in FIG. 5b) when the command signal to open the valve 15 is delivered to the circuit 37p. When such command signal is not applied or when the output p of the interface 33 assumes a low level L, the gates A5 and A6 in the circuit 37p are both disabled, whereby a low level L commanding the valve to be closed is applied to the solenoid driver 27.

The lower half of the table shown in FIG. 5c indicates valve energizing signals applied by the circuit 37n to the driver 28 in a manner corresponding to the pressure detected by the sensor 23 (regions ④, to ⑦, shown in FIG. 5b) when the command signal to open the valve 20 is delivered to the circuit 37n.

When such command signal is not applied or when the output n of the interface 33 assumes a low level L, the gates A5 and A6 in the circuit 37n are both disabled, whereby a low level L commanding the valve to be closed is applied to the solenoid driver 28.

As mentioned previously, in response to IN1 interrupt pulse and IN2 interrupt pulse from the master unit 60, CPU 34 alternately develops the command signals to open the valves 15 and 20 and apply them to the digitized pressure regulating circuits 37p and 37n, respectively. In response to R-positive pressure data (d=Prp) from the master unit 60, CPU 34 latches it in the latch 36p. In response to R-negative pressure date (g=Prn) received from the master unit 60, CPU 34 latches it in the latch 36n.

Figure 6:
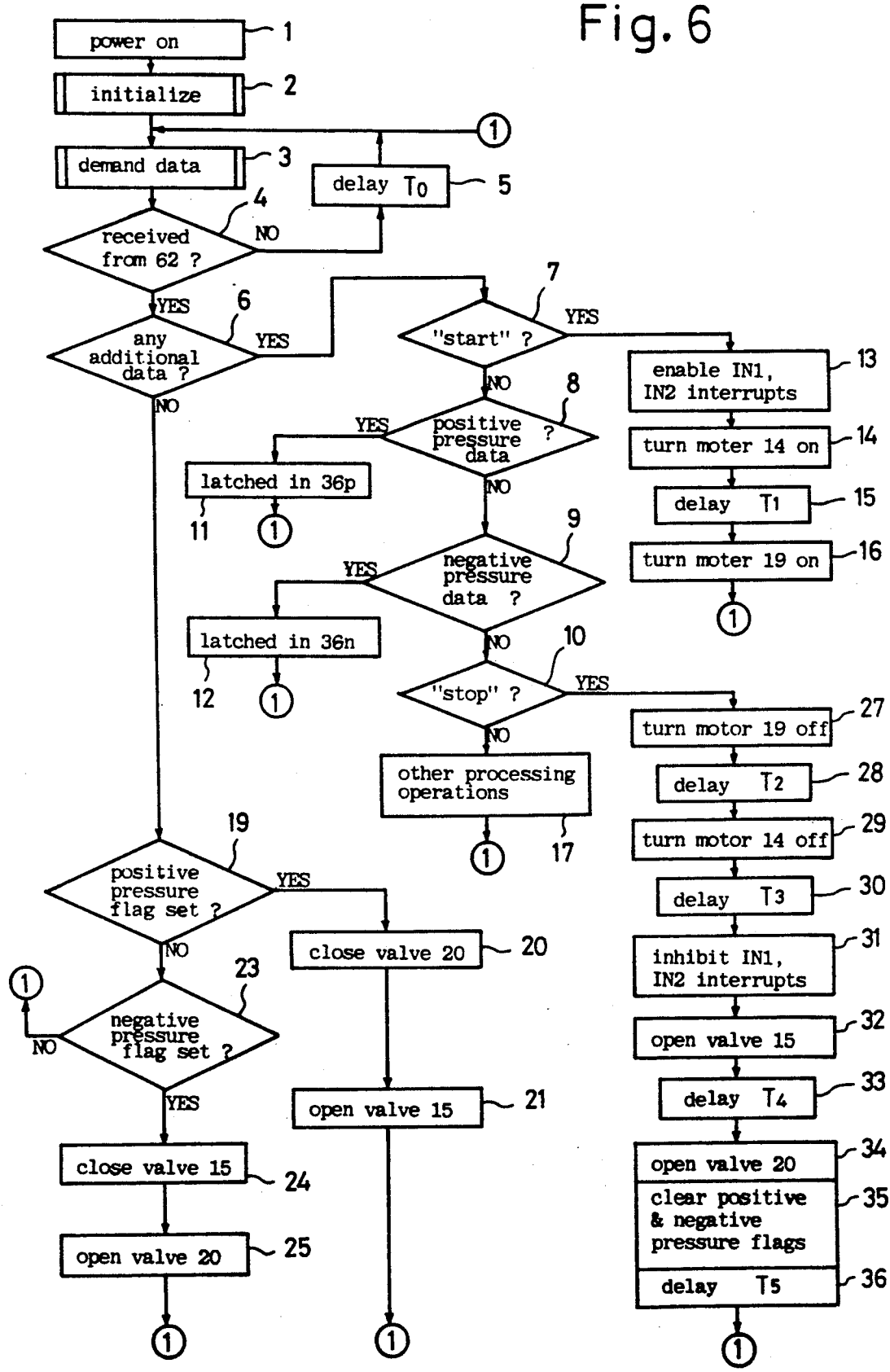
FIG. 6 is a flowchart of control operation by CPU 34 shown in FIG. 4.

FIG. 6 is a flowchart illustrating a control operation by CPU 34 of the drive unit 10 which drives the right-hand artificial heart 11R. It is to be understood that the interrupt operation performed by CPU 34 in response to timing pulses (IN1 and IN2 interrupt pulses for R) from the master unit 60 remains the same as that illustrated in FIGS. 2b and 2c.

Referring to FIG. 6, when the power is turned on (1), CPU 34 presets signals at its input and output ports to their standby condition or off condition (15, 20, 14 and 19), clears internal timers, counters, registers and flags, and inhibit IN1 and IN2 interrupts (2). CPU 34 then demands data from CPU (not shown) of the master unit 60 (3).

A data transfer between CPU 34 and CPU of the master unit 60 takes place in terms of a frame comprising start bits, data, end bits and error check bits. During the data demand at the step 3, CPU 34 places data representing "ready" in the "data" term item of the frame. Upon receiving one frame from CPU 34, CPU of the master unit 60 places any data which is then to be transmitted to CPU 34 into the "data" item of one frame for transmission to CPU 34. When it has no data to be transmitted, meaning that a current status is to be maintained, CPU of the unit 60 places "ACK" (acknowledge) in the "data" item of the frame for transmission.

Upon demanding data from CPU of the unit 60 (3), CPU 34 presets a timer $T_0$ (program timer) and waits for its time-out (5). If it receives a transmission from CPU of the unit 60 before the time-out, the program proceeds to step 6. When there is no transmission, it transmits another frame to CPU of the unit 60.

The operation of CPU 34 and CPU of the unit 60 will now be described in a manner corresponding to a key operation on an operating board (not shown) of the unit 60 by an operator.

I. When an operator enters R-positive pressure on the operating board, CPU of the unit 60 transmits it to CPU 34, which then proceeds through steps 4, 6, 7, 8 and 11, latching it in a latch 36p at step 11. This takes place by switching a data selector 35 to the output of the latch 36p and delivering R-positive pressure data and a latch command pulse to the data selector 35. L-positive pressure is similarly preset in the drive unit 50.

II. When an operator enters R-negative pressure on the operating board, CPU of the unit 60 transmits it to CPU 34, which upon receiving it, proceeds through steps 4, 6, 7, 8, 9 and 12, latching R-negative pressure in the latch 36n at step 12. This takes place by switching the data selector 35 to the output of the latch 36n and delivering R-negative pressure and latch command pulse to the data selector 35. L-negative pressure is similarly preset in the drive unit 50.

III. When no cardiograph is used, CPU of the unit 60 calculates the period Th of heartbeat, R systole period Trc and L systole period Tlc on the basis of R ratio, L ratio and the heart rate (the number of heartbeats per minute) which are inputted from the operating board. It develops a pulse (IN1 interrupt pulse for R) with a period Th by a timer control, and applies it to IN1 interrupt port of CPU 34. It also develops another pulse (IN2 interrupt pulse for R) which is delayed by Trc from the IN1 interrupt pulse and applies it to IN2 interrupt port of CPU 34. CPU of the master unit 60 also calculates a phase displacement Tpd of L relative to R on the basis of phase displacement data which is input from the operating board, and develops a pulse (IN1 interrupt pulse for L) having a phase displacement of Tpd relative to IN1 interrupt pulse for R, and applies it to the drive unit 50. It also develops another pulse (IN2 interrupt pulse for L) which is delayed by Tlc with respect to IN1 interrupt pulse for L, and also applies it to the drive unit 50. The generation of these pulses extends from a point immediately before the occurrence of a "start" command until immediately after a "stop" command. If there is updated input from the operating board during the generation of these pulses, the described operation is performed again to update the timing of developing the pulses.

Where a cardiograph is used, CPU of the master unit 60 develops IN1 interrupt pulse for R as having a time delay, which is input from the operating board, with respect to a cardiographic wave (pulse) which occurs with the period of the heartbeat. Other pulses are developed as referenced to this IN1 interrupt pulse.

IV. When a "start" command is entered on the operating board and CPU of the master unit 60 responds thereto by transmitting a "start" command to CPU 34, the latter proceeds through steps 4, 6, 7 and 13, enabling IN1 and IN2 interrupts (13), delivering a signal which commands the energization of the compressor motor 14 to the motor driver 25 or delivering such signal to an output port thereof (14), waits for a time duration $T_1$, during which a transient high current occurs due to the starting of the motor, to pass (15) and then delivers a signal which commands the energization of the decompressor motor 19 to the motor driver 26 after the time duration $T_1$ has passed (16). The program then proceeds to the data demand step 3. CPU of the master unit 60 also provides a "start" command to the drive unit 50, the microprocessor (not shown) of which operates in the same manner as CPU 34.

Since the interrupt operation is enabled at step 13, when CPU of the master unit 60 applies IN1 interrupt pulse for R to an input port IN1 of CPU 34 and applies IN2 interrupt pulse for R to interrupt port IN2 of CPU 34, the latter responds thereto by executing IN1 interrupt subroutine (37) shown in FIG. 2b or executing IN2 interrupt operation (40) shown in FIG. 2c. This takes place until IN1 and IN2 interrupt operations are inhibited (31).

In response to IN1 interrupt pulse for R, CPU 34 enters IN1 interrupt subroutine (37) shown in FIG. 2b where it clears the negative pressure flag (data indicating the diastole) (38) and sets the positive pressure flag (data indicating the systole) (39). The program then returns to the main routine (FIG. 6) at a point which immediately precedes the interrupt subroutine (37).

In response to IN2 interrupt pulse for R, CPU 34 enters IN1 interrupt subroutine (40) shown in FIG. 2c where it clears the positive pressure flag (41) and sets the negative pressure flag. The program then returns to the main routine at a point immediately preceding the interrupt subroutine (40).

CPU of the master unit 60 delivers IN1 and IN2 interrupt pulses for L to the drive unit 50, CPU of which executes the interrupt operation in the similar manner as CPU 34 (see FIGS. 2*b* and 2*c*). CPU of the drive unit 50 operates in the similar manner as CPU 34. Since the drive unit 50 is constructed and operates in the same manner as the drive unit 10, the ensuing description only covers the drive unit 10.

V. Returning to FIG. 6, when the compressor motor 14 and the decompressor motor 19 are energized in response to the "start" command, CPU 34 executes the data demand (3), receives one frame of data from CPU of the master unit 60 (4), and since there is no additional data or parameter data in the transmitted frame unless updated input or a change in the operating parameters is input from the operating board (6), executes a "switching control" comprising the steps 19 to 25, after which the program returns to the data demand step 3.

Unless a fresh input is entered from the operating board, CPU of the master unit 60 does not transmit parameter data (it only transmits "ACK" in response to the data demand (3)). Accordingly, CPU 34 loops around the steps 3, 4, 6, 19 to 25 and 3, thus repeating the "switching control" comprising the steps 19 to 25 with a substantially constant period.

VI. During the "switching control" comprising the steps 19 to 25, it is initially examined if the positive or the negative flag is set (19, 23). If neither flag is set, this means that the "start" command has not been issued yet, and accordingly the program returns to the step 3 without substantial execution of the "switching control".

If the positive pressure flag is set as by the IN1 interrupt subroutine (37) shown in FIG. 2*b*, this signifies that it is now in the systole or a time interval during which the valve 15 is commanded to be opened, namely, from the occurrence of IN1 interrupt pulse to the occurrence of IN2 interrupt pulse. In this instance, a command signal which requires the solenoid valve 20 to be turned off is applied to the output port n of the interface 33 (20), and a command signal to open the solenoid valve 15 is applied to the output port p of the interface 33.

When the negative pressure flag is set as by the IN2 interrupt subroutine (40) shown in FIG. 2*c*, this signifies that it is now in the diastole or time interval during which the valve 20 is to be opened, namely, from the occurrence of IN2 interrupt pulse to the occurrence of IN1 interrupt pulse. In this instance, a command signal to turn the solenoid valve 15 off is applied to the output port p of the interface 33 (24), and the command signal to open the valve 20 or to energize the electrical coil of the solenoid valve 20 is applied to the output port n of the interface 33 (25).

As a result of the "switching control", the signals "33-p" and "33-n" shown in FIG. 5*b* are applied to the digitized pressure regulating circuits 37*p* and 37*n*, respectively. In response to these signals, the circuits 37*p* and 37*n* regulate the pressure in the manner mentioned above. Thus, during the systole when the positive pressure flag is set, the solenoid valve 20 is closed while the solenoid valve 15 is opened and closed so that the pressure detected by the sensor 23 is equal to R-positive pressure (d). During the diastole when the negative pressure flag is set, the solenoid valve 15 is closed while the solenoid valve 20 is opened and closed so that the pressure detected by the sensor 23 is equal to R-negative pressure (g). In this manner, a constant positive and negative pressure control as well as a switching between a positive/negative pressure can be achieved by providing the single solenoid valve 15 or 20 in the positive or the negative pressure system, respectively.

VII. During the execution of the "switching control" mentioned under the paragraph VI during which the artificial hearts 11R and 11L are being driven, any input entered on the operating board of the master unit 20 causes such data to be transmitted to CPU 34 from CPU of the unit 20 in the similar manner as mentioned under the paragraphs I and II. CPU 34 updates the content of the latches 36*p* and 36*n* with the data received, and CPU of the master unit 60 re-calculates the timing so as to modify the interrupt pulses in accordance with the re-calculated data. Accordingly, the "switching control" mentioned under the paragraph VI is based on such modified data and pulses.

VIII. When an operator enters a "stop" command on the operating board of the master unit 60, CPU thereof transmits such command to CPU 34. Upon receiving such command, CPU 34 proceeds through steps 4, 6, 7, 8, 9, 10 and 27, deenergizing the decompressor motor 19 (27), waiting for the transient stop period $T_2$ to pass (28), whereupon the compressor motor 14 is stopped (29), and after an associated transient stop period $T_3$ to pass (30), IN1 and IN2 interrupts are inhibited (31). Because IN1 and IN2 interrupt subroutines (FIGS. 2*b* and 2*c*) are no longer executed or the flags cease to be updated, the artificial heart 11R ceases to operate. Subsequently, CPU 34 turns the solenoid valve 15 on (32), waits for a transient period $T_4$ associated with the energization of its coil to pass (33), and then turns the solenoid valve 20 on (34). As a result of the both solenoid valves 15 and 20 being turned on, the compressed air from the positive pressure accumulator 16 flows into the negative pressure accumulator 21, allowing the pressures within the both accumulators 16, 21 to approach the atmospheric pressure. CPU 34 then clears the positive and the negative pressure flag (35), and waits for a sufficient time period $T_5$ which allows the pressures of the both accumulators to neutralize (36) before advancing to the data demand step 3.

As mentioned, the valve 15 is maintained open until the detected pressure reaches the first given value (a) during the systole, thus achieving a rapid rise in the pressure which is applied to the artificial heart 11R. When the first given pressure is exceeded, the valve 14 is opened and closed with a duty cycle of 75%, thus providing a more gentle pressure rise. When R-positive pressure (d) is exceeded, the valve 14 is opened and closed with a duty cycle of 25%, whereby the pressure which has been rising then begins to decline in a gentle manner. In this manner, it is possible to stabilize the pressure at R-positive pressure (d) smoothly without producing any excessive overshoot during the rising period of the positive pressure. Any significant pressure fluctuation is also avoided during the stable period which follows the rising period. This is because of the inertia of the valve 15 which involves a time lag in the opening and closing thereof with respect to the energization and deenergization of the associated coil.

During the systole, when the region (e) immediately before the target pressure (d) which exceeds a first given value (e) is reached, the valve 15 is opened and closed in an oscillating manner with a duty cycle of 75%, thus accompanying a reduced rate in the rise of the positive pressure. If the opening and closing operation of the valve 15 is switched to produce a declining pressure when the target pressure (d) is reached, the occurrence of an overshoot as in the prior art is eliminated. In the region ② which has just exceeded the target pressure (d), the valve 15 is opened and closed in an oscillating manner with a duty cycle of 25%, producing a retarded declining rate in the positive pressure. Accordingly, if the opening or closing operation of the valve 15 is switched to the rising pressure when the target pressure (d) is reached, the occurrence of an excessive undershoot is experienced in the prior art is eliminated. Also during the diastole, the valve 20 is opened and closed in an oscillating manner in the regions ⑤0 and ⑥ around the target pressure (g).

It is to be noted that the solenoid valves 15 and 20 will be fully open when their associated coils are energized with a duty cycle of 100%. Utilizing the energization with a duty cycle of 75% and at the frequency of 200 Hz, the on/off energization which causes the energization to be interrupted before the valve reaches its fully open position causes the valve opening to be on the order of 70% as viewed in a time sequence. The valve opening will be on the order of 20% for the energization with a duty cycle of 25%.

Third Embodiment

Figure 7:
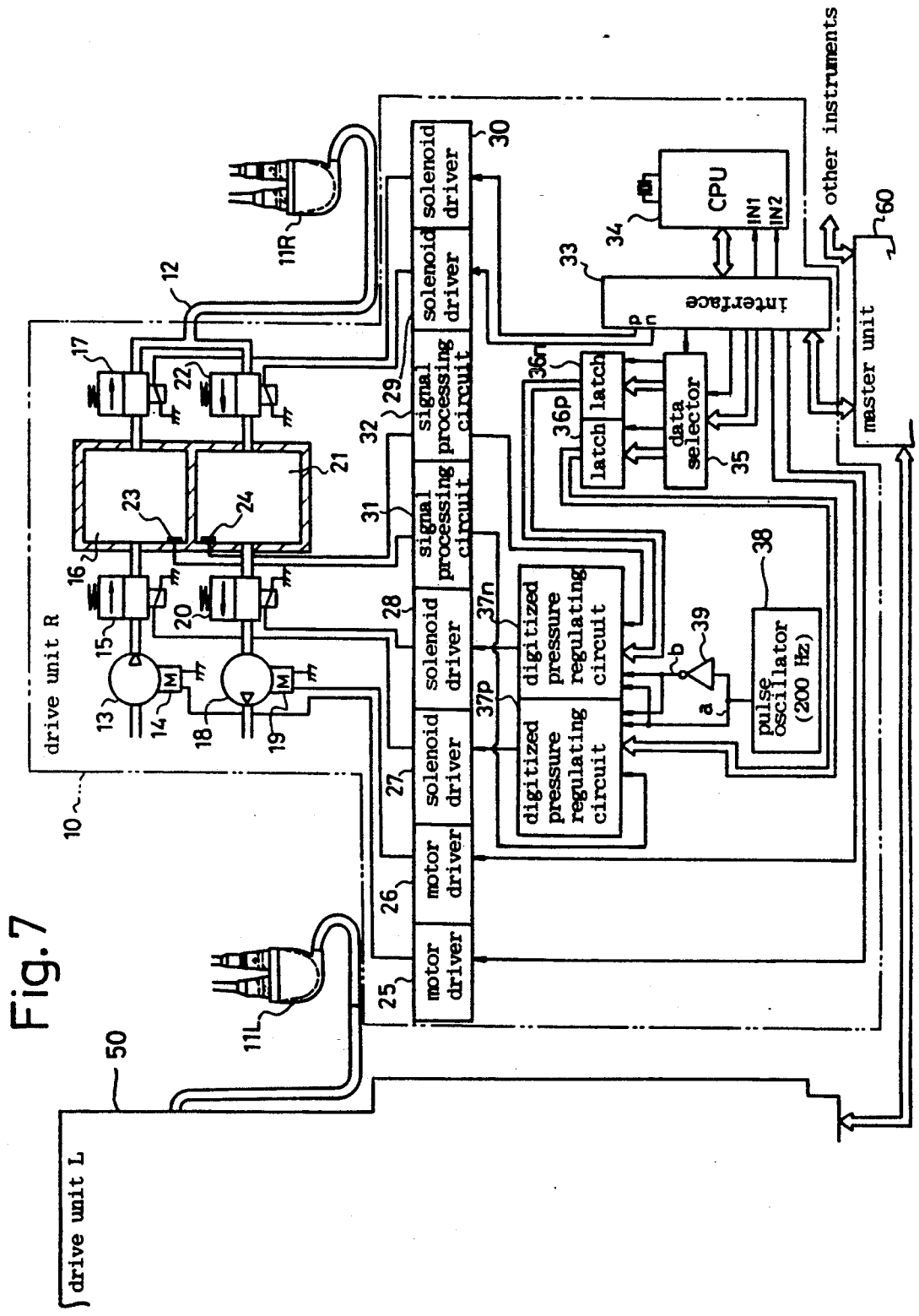
FIG. 7 is a block diagram of a third embodiment of the invention.

In a third embodiment shown in FIG. 7, a positive pressure system includes a positive pressure regulating solenoid valve 15, a positive pressure accumulator 16 and a positive pressure open/close solenoid valve 17 while a negative pressure system includes a negative pressure regulating solenoid valve 20, a negative pressure accumulator 21 and a negative pressure open/close solenoid valve 22, generally in the similar manner as disclosed in U.S. Pat. No. 4,546,760. A first pressure sensor 23 detects the pressure in the accumulator 16 while a second pressure sensor 24 detects the pressure within the accumulator 21. In this embodiment of the invention, both the positive and the negative pressure accumulator 16, 21 have a reduced capacity on the order of 300 cc.

Figure 8:
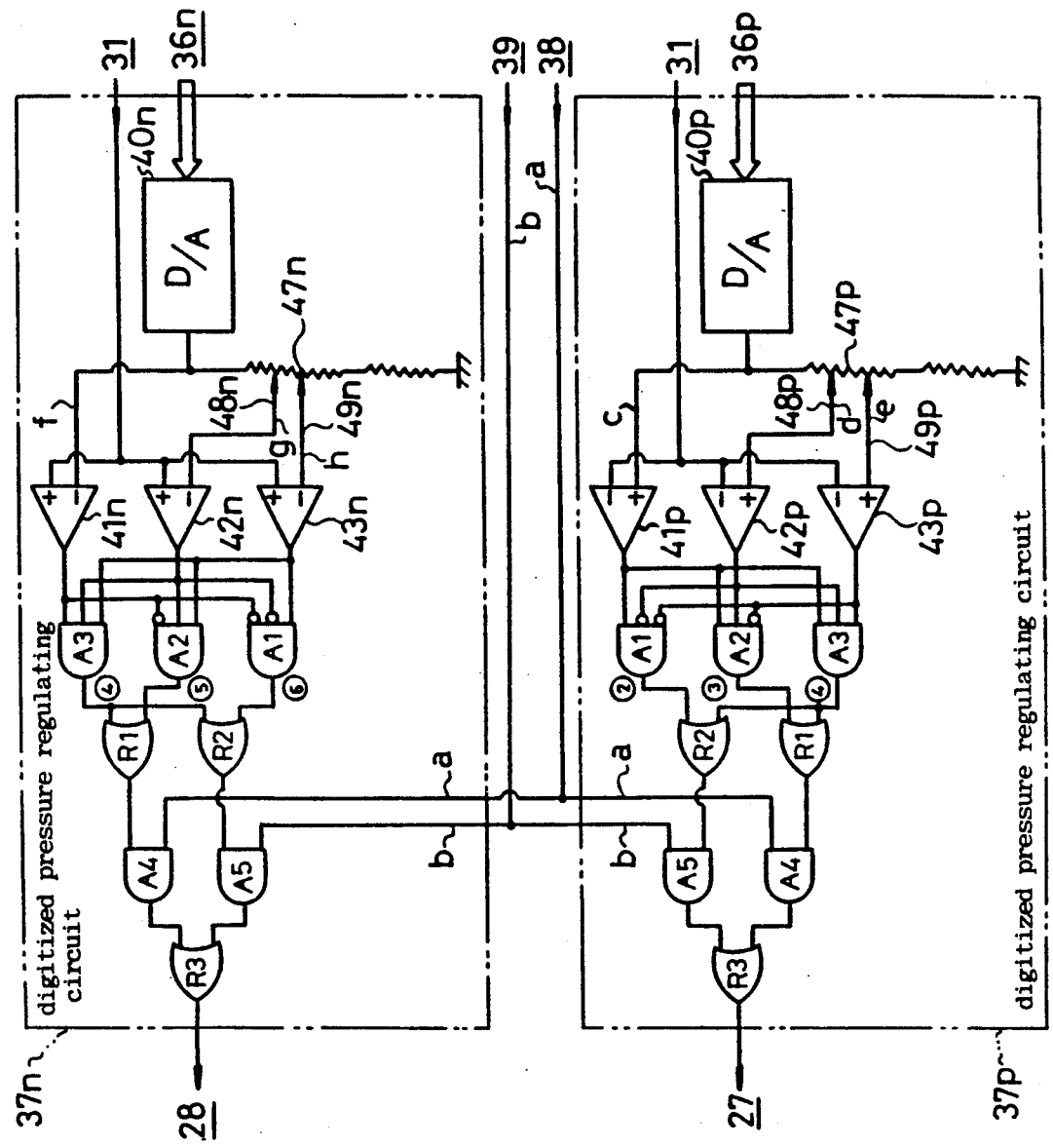
FIG. 8 is a block diagram of digitized pressure regulating circuits 37p and 37n shown in FIG. 7.

In the third embodiment, the solenoid valves 17 and 22 are connected through associated solenoid drivers 30 and 29, respectively, so as to be energized with a systole signal "33-p" appearing on an output port p and a diastole signal "33-n" appearing on an output port n of an interface 33. Digitized pressure regulating circuits 37p and 37n are illustrated in FIG. 8 where it will be noted that the signals "33-p" and "33-n" are not applied thereto. Consequently, the digitized pressure regulating circuit 37p delivers signals appearing on the upper half of the table shown in FIG. 5c to the solenoid driver 27 in a manner corresponding to the pressures (① to ④) shown in FIG. 5b detected by the first pressure sensor 23 without regard to the systole or the diastole period. Also the digitzed pressure regulating circuit 37n delivers the signals appearing on the lower half of the table of FIG. 5c to the solenoid driver 28 in a manner corresponding to the pressures (④ to ⑦) shown in FIG. 5b detected by the second pressure sensor 24, again without regard to the systole or the diastole period.

The operation of the master unit 60 and CPU 34 remains entirely the same as the operation of the second embodiment described above in connection with FIG. 4, with a similar effect.

In either the second or the third embodiment, regions ③ and ⑤ in which the pressure is gently increased as well as regions ② and ⑥ in which the pressure is gently decreased are established across the target pressures (g,g) in order to suppress an overshoot or undershoot which might occur immediately below or above the target pressures and to achieve a pressure which is equivalent to a selected target pressure in an accurate and precise manner. It will be noted that in the prior art practice, maximum pressure deviations are manifest as an overshoot during a pressure rise when switching from the diastole to the systole and an undershoot (which is equivalent to an overshoot as viewed in terms of the absolute magnitude of the pressure) during a pressure fall when switching from the systole to the diastole, both of which represented a significant problem, and the suppression of which would provide a great advantage. This end may be attained by providing D/A converters 40p and 40n in the digitized pressure regulator circuits 37p and 37n which directly deliver target pressures d=Prp and g=Prn; comparators 41p and 41n, and AND gate A3 and OR gates R1 and R2 may be omitted so that an output from the gate A2 is directly applied to AND gate A4; target pressures d=Prp and g=Prn may be fed to the comparators 42p and 42n, respectively while the first given value a and the second given value f may be fed to the comparators 43n and 43p, respectively. With this arrangement, when the pressures in the region ② and ⑥ are detected, the valves 15 and 20 will be closed. Since the rate of pressure rise in the regions ③ and ⑤ is low, an overshoot when switching from the diastole to the systole or vice versa can be suppressed.

The compressor 13 is provided with a relief valve which establishes a communication between its discharge port and the atmosphere at a pressure which is by a given amount higher than the target pressure (d). The decompressor 13 is provided with a relief valve which establishes a communication between its suction port and the atmosphere at a pressure which is by a given value less than the target pressure (g). In the second embodiment, these bleed valves may comprise solenoid valves, which can be served by the pressure regulator solenoid valves 15 and 20. In this instance, the "closed/open condition of solenoid valve 15" is equivalent to "establishment/interruption of a communication of the discharge port of the compressor 13 with the atmosphere"; and the "closed/open condition of the solenoid valve" is equivalent to the "establishment/interruption of a communication of the suction port of the decompressor 18 with the atmosphere".

As described, it will be seen that the arrangement of both the second and the third embodiments allow the capacity of the accumulators to be reduced and are also capable of suppressing a variation in the magnitude of a positive/negative pressure fed to the pumping unit (11R).

In the above description, the pumping unit has been illustrated as an artificial heart. However, it should be understood that the invention is equally applicable to other pumping units used in connection with a living human body or industrial pumping units which operate in the similar manner as the artificial heart 11R.

What we claim is:

1. A pumping drive unit for driving a pumping unit, the pumping unit having a drive chamber, said pumping drive unit comprising:
 a source of positive pressure;
 a source of negative pressure;
 a single positive pressure open/close valve unit interposed between the drive chamber of the pumping unit and the source of positive pressure;

a single negative pressure open/close valve unit interposed between the drive chamber of the pumping unit and the source of negative pressure;

fluid connecting means interconnecting the positive and negative open/close valve units with the drive chamber of the pumping unit;

pressure detecting means for detecting a fluid pressure in said fluid connecting means which extends from the positive and the negative pressure open/close valve units to the drive chamber of the pumping unit; and drive pressure control means operative during a preset systole of the pumping unit to close the negative pressure open/close valve unit and to close or open the positive pressure open/close valve unit responsive to the fluid pressure in said fluid connecting means as detected by the pressure detecting means relative to a first predetermined pressure value to maintain the positive pressure supplied to the pumping unit at said first predetermined pressure value and said drive pressure control means oiperative during a preset diastole of the pumping unit to close said positive pressure open/close valve unit and to close or open the negative pressure open/close valve unit responsive to the fluid pressure in said fluid connecting means as detected by the pressure detecting means relative to a second predetermined pressure value to maintain the negative pressure supplied to the pumping unit at said second predetermined pressure value; wherein the drive pressure control means is operative during a preset systole of the pumping unit to close the positive pressure open/close valve unit when the fluid pressure detected by the pressure detecting means is equal to or greater than a first predetermined pressure value and to open the positive pressure open/close valve unit when the fluid pressure detected by the pressure detecting means is less than the first predetermined pressure value and operative during a preset diastole of the pumping unit to close the negative pressure open/close valve unit when the fluid pressure detected by the pressure detecting means is equal to or less than a second predetermined pressure value and to open the negative pressure open/close valve unit when the fluid pressure detected by the pressure detecting means exceeds the second predetermined pressure value.

2. A pumping drive unit as defined in claim 1 in which the source of positive pressure includes a positive pressure accumulator and a pump for sup-plying a fluid having a positive pressure to the positive pressure accumulator, and the source of negative pressure includes a negative pressure accumulator and a pump for drawing a fluid from the negative pressure accumulator.

* * * * *

UNITED STATES PATENT AND TRADEMARK OFFICE
CERTIFICATE OF CORRECTION

PATENT NO.  : 5,147,392

DATED       : September 15, 1992

INVENTOR(S) : Yoshitaka INAGAKI, Akira SUZUKI, Sadahiko MUSHIKA

It is certified that error appears in the above-identified patent and that said Letters Patent is hereby corrected as shown below:

Title page, item:

[57]  ABSTRACT, line 3, change "aa" to -- a --.

Signed and Sealed this

Twenty-first Day of December, 1993

Attest:

BRUCE LEHMAN

*Attesting Officer*    *Commissioner of Patents and Trademarks*